(12) United States Patent  
Broome et al.

(10) Patent No.: US 8,454,615 B2
(45) Date of Patent: Jun. 4, 2013

(54) COMBINATION DIRECTIONAL AND NON-DIRECTIONAL BONE TAMP

(75) Inventors: Charles Brandon Broome, Greer, SC (US); Mojan Goshayeshgar, Atherton, CA (US)

(73) Assignee: Kyphon Sarl, Neuchatel (CH)

( * ) Notice: Subject to any disclaimer, the term of this patent is extended or adjusted under 35 U.S.C. 154(b) by 19 days.

(21) Appl. No.: 13/176,397

(22) Filed: Jul. 5, 2011

(65) Prior Publication Data

US 2013/0013007 A1     Jan. 10, 2013

(51) Int. Cl.
*A61F 2/46*     (2006.01)
(52) U.S. Cl.
USPC ..................................... 606/86 R
(58) Field of Classification Search
USPC ..... 606/79–86 R, 86 A, 99; 623/17.11–17.16
See application file for complete search history.

(56) References Cited

U.S. PATENT DOCUMENTS

| 5,084,010 | A | 1/1992 | Plaia et al. |
| 6,979,341 | B2 * | 12/2005 | Scribner et al. ............... 606/192 |
| 2002/0099385 | A1 * | 7/2002 | Ralph et al. ..................... 606/92 |
| 2005/0090852 | A1 * | 4/2005 | Layne et al. .................. 606/190 |
| 2006/0264945 | A1 * | 11/2006 | Edidin et al. .................... 606/63 |
| 2008/0065020 | A1 | 3/2008 | Ralph et al. |
| 2010/0274180 | A1 | 10/2010 | Donovan et al. |
| 2011/0106007 | A1 | 5/2011 | Auyoung et al. |

OTHER PUBLICATIONS

International Search Report and Written Opinion for PCT/US2012/045484 the counterpart application mailed on Jan. 23, 2013.

* cited by examiner

*Primary Examiner* — Matthew Lawson
(74) *Attorney, Agent, or Firm* — Sorell, Lenna and Schmidt LLP (57) ABSTRACT

A minimally invasive surgical system can include a cannula having a side port and an open distal end, and an expandable bone tamp. The bone tamp includes an elongate shaft coupled to an expandable element. The elongate shaft has a length adapted to align the expandable element with the side port or extend the expandable element completely beyond the distal opening of the cannula. In this manner, the cannula and bone tamp enable either directional (i.e., through the side port) or non-directional (i.e., completely outside the cannula) bone tamping.

15 Claims, 11 Drawing Sheets

COMBINATION DIRECTIONAL AND NON-DIRECTIONAL BONE TAMP

FIELD OF THE INVENTION

The invention relates to a system and method for performing a surgical procedure, and in particular, to a percutaneous bone manipulation system that enables both directional and non-directional bone manipulation.

BACKGROUND OF THE INVENTION

A minimally invasive procedure is a medical procedure that is performed through the skin or an anatomical opening. In contrast to an open procedure for the same purpose, a minimally invasive procedure will generally be less traumatic to the patient and result in a reduced recovery period.

However, there are numerous challenges that minimally invasive procedures present. For example, minimally invasive procedures are typically more time-consuming than their open procedure analogues due to the challenges of working within a constrained operative pathway. In addition, due to the specialized instruments required for such procedures, efforts to enable flexibility/adaptability in the face of varying surgical scenarios can significantly increase the number (and hence, cost) of a given minimally invasive surgical system.

For example, vertebral compression fractures (VCFs) are now commonly treated by percutaneously positioning a bone tamp into the fractured vertebral body, inflating the bone tamp to create a void in the cancellous bone and potentially restore the vertebral body height, and then filling the void with a bone filler material (e.g., polymethylmethacrylate, or PMMA). This procedure is known as kyphoplasty.

Typically, kyphoplasty is performed using a non-directional bone tamp—i.e., a balloon catheter that expands radially about a central axis. However, depending on the nature of the VCF and/or the condition of the cancellous bone within the vertebral body, a directional bone tamp that expands radially in some directions but not others can improve procedure efficacy. Typically, non-directional bone tamps and directional bone tamps are separate devices, and only non-directional bone tamps are typically included in standard kyphoplasty kits to minimize kit costs. However, this undesirably reduces physician flexibility when performing a kyphoplasty procedure, and also increases procedure cost whenever a directional bone tamp is required.

Accordingly, it is desirable to provide surgical tools and techniques that enable both non-directional and directional bone manipulation using the same instruments.

SUMMARY OF THE INVENTION

By pairing a cannula having both a side port and an open distal end with an expandable bone tamp that is extendable out the open distal end of the cannula, both non-directional and directional bone manipulation can be performed using the same bone tamp.

In one embodiment, a system for performing a surgical procedure can include a cannula and an expandable bone tamp. The cannula can include a sidewall defining an interior lumen and open proximal and distal ends, wherein the sidewall also defines at least one partial circumferential opening (i.e., a side port) that is sized to allow at least partial expansion of an expandable element of the bone tamp therethrough. The bone tamp includes an elongate shaft having a length adapted to enable alignment of the expandable element with the side port or deployment of the expandable element completely beyond the distal opening of the cannula (i.e., extending the expandable element out the cannula through the open distal end). In this manner, the cannula and bone tamp enable either directional (i.e., through the side port) or non-directional (i.e., completely outside the cannula) bone tamping, as desired by the physician.

In various embodiments, the expandable element of the bone tamp can be an inflatable element (e.g., balloon(s) or bag(s)), a mechanically expanding construct, and/or a deforming structure. When implemented with a inflatable element, the elongate shaft can be a single shaft through which inflation fluid can be delivered to the inflatable element, or in various other embodiments, the elongate shaft can at least partially enclose an inner shaft, such that an inflation fluid delivery lumen is defined between the two shafts or within the inner shaft. In various other embodiments, an inflatable bone tamp can further include a stiffening stylet sized to fit within the elongate shaft and/or the inner shaft (either fixedly or removably).

In various other embodiments, the bone tamp can include one or more markers to indicate the position and/or orientation of the expandable structure relative to one or more features of the cannula (e.g., the side port, the open distal end, and/or any other cannula elements). In some embodiments, markers on the elongate shaft can indicate when the expandable structure is aligned with the side port and/or extended past the open distal end of the cannula. In some embodiments, the markers can be visual markings, and in various other embodiments, the markers can be physical features (e.g., detents, notches, teeth, movable or removable stops, etc.) that stop ingress of the elongate shaft into the cannula when a desired positioning of the expandable element relative to the cannula is achieved.

In some embodiments, the bone tamp can include an elongated distal tip that extends beyond the distal end region of the expandable element. This elongated distal tip can engage with the portion of the cannula distal to the side port, thereby enhancing the stability of the interface between the bone tamp and the cannula during directional expansion through the side port. In various embodiments, the elongated distal tip is at least half as long as the expandable element to ensure a solid interface with the cannula. In various other embodiments, the elongated distal tip can be shortened and the elongate shaft, optional inner shaft, and/or optional stylet can be formed from materials rigid/stiff enough to maintain stability during directional expansion even with the shorter distal tip length.

In various other embodiments, the system can further include accessory instruments such as an access cannula (sized to allow insertion of the side port cannula), an introducer, a guide pin, a drill, a curette, an access needle, In various other embodiments, the system can further include a material delivery nozzle for the delivery of bone filler material. In some embodiments, the material delivery nozzle can be sized to fit at least partially through the side port cannula, thereby enabling bone filler material delivery through the side port and/or beyond the open distal end of the cannula.

In various other embodiments, the system can further include instructions for performing a surgical procedure using the cannula and the bone tamp. In one embodiment, the instructions can describe the use of the cannula and bone tamp to treat a fracture (e.g., in a vertebra, the tibial plateau, the calcaneus, the distal radius, the proximal humerus, the femoral head, and/or other fracture sites) by positioning the cannula with either the side port or open distal end adjacent to the fracture, and then inserting the bone tamp into the cannula and expanding the expandable element through the side port or extending the expandable element out the open distal end before expanding, respectively, to reduce the fracture and/or create a void to enable controlled, contained reinforcement with bone filler material. In various embodiments, the instructions can optionally describe expanding the expandable element multiple times and/or in multiple locations/orientations/directions. In various other embodiments, the instructions can further describe removing the bone tamp from the cannula and delivering bone filler material to the region of bone tamped by the expandable element.

As will be realized by those of skilled in the art, many different embodiments of an inflatable bone tamp incorporating an inner shaft having a predetermined extensible region(s), and systems, kits, and/or methods of using such an inflatable bone tamp according to the present invention are possible. Additional uses, advantages, and features of the invention are set forth in the illustrative embodiments discussed in the detailed description herein and will become more apparent to those skilled in the art upon examination of the following.

DETAILED DESCRIPTION

By pairing a cannula having both a side port and an open distal end with an expandable bone tamp that is extendable out the open distal end of the cannula, both non-directional and directional bone manipulation can be performed using the same bone tamp.

Figure 1:
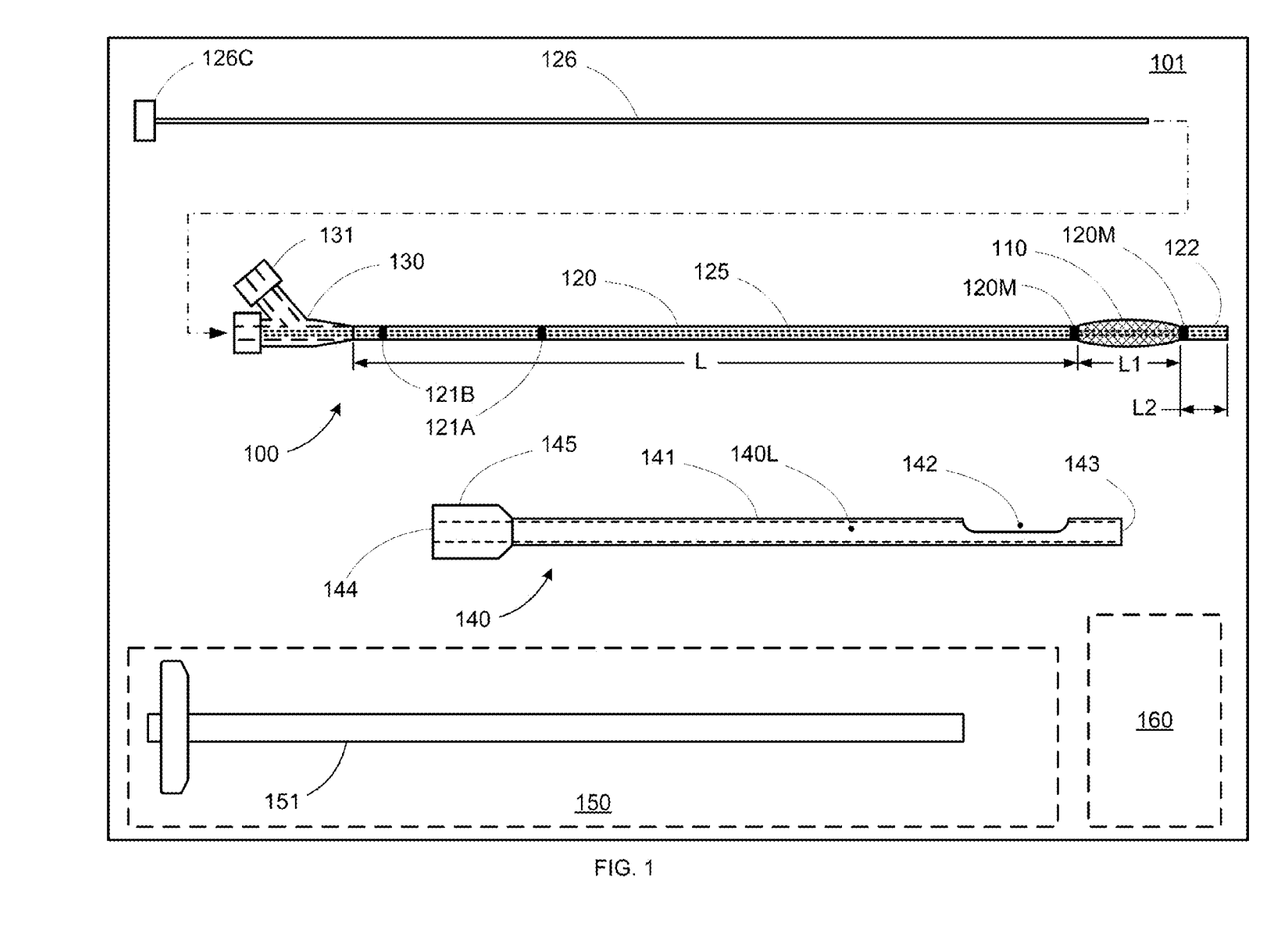
FIG. 1 shows a surgical kit that incorporates an expandable bone tamp and a cannula that can be used in conjunction to provide either directional or non-directional bone tamping, as desired by the physician.

FIG. 1 shows a diagram of a kit 101 for use in performing a minimally invasive surgical procedure. Kit 101 includes an expandable bone tamp 100 and a cannula 140. Expandable bone tamp 100 includes an expandable structure 110 (e.g., an inflatable structure such as a balloon, or a mechanically expandable or deformable structure) mounted on the distal end of an elongate shaft 120. Expandable structure 110 is configured such that when in an unexpanded state, expandable structure 110 can be driven through an inner lumen 140L of cannula 140 by elongate shaft 120.

Cannula 140 includes a shaft 141 that defines the inner lumen 140L extending between a proximal opening 144 and a distal opening 143 of cannula 140. Shaft 141 also includes at least one cutout in its sidewall that defines a side port 142 (i.e., a partial circumferential opening in the sidewall of cannula 140) in communication with inner lumen 140L. Side port 142 is sized such that expandable structure 110 can be expanded at least partially through side port 142.

Note that while a single side port 142 is depicted for exemplary purposes, in various other embodiments, cannula 140 can incorporate any number of side ports. Note further that while cannula 140 would typically exhibit a tubular construction having a circular cross section, in various embodiments cannula 140 can have a square, rectangular, oval, irregular, or any other cross sectional configuration.

In addition, shaft 120 of bone tamp 100 has a length such that when inserted through proximal opening 144, expandable structure 110 can be extended out through distal opening 143. In various embodiments, bone tamp 100 can include an optional elongate distal tip 122 beyond the distal end of expandable structure 110 to facilitate engagement of bone tamp 100 with cannula 140, as described in greater detail below.

In some embodiments, bone tamp 100 can include one or more positioning features 121 for indicating the position of expandable structure 110 relative to cannula 140. For example, as depicted in FIG. 1, bone tamp 100 includes features 121A and 121B that when aligned with proximal opening 144, indicate that expandable structure is aligned with side port 142 or extended beyond distal opening 143 of cannula 140, respectively. Note that while positioning features are depicted as markings on shaft 120 for exemplary purposes, in various other embodiments, positioning features 121 can be physical features (e.g., a movable stop that can be positioned along shaft 120 to stop ingress of bone tamp 100 into cannula 140 when expandable structure 110 is positioned at side port 142 and/or out of distal opening 143). In some embodiments, features 121 can further indicate the orientation of bone tamp 100 relative to cannula 140 (e.g., rather than a solid mark encircling shaft 120, features 121 could one or more tic marks on shaft 120 that correspond with particular orientations of expandable structure 110).

As noted above, in various embodiments, expandable structure 110 can be an inflatable structure such as a balloon or bag. In such a construction, expandable structure 110 can be formed from any type of inflatable material, including non-compliant materials (e.g., many Nylon and polyethylene materials), semicompliant materials (e.g., many polyurethane materials), compliant materials (e.g., latex rubber), or any combination thereof.

Expandable structure 110 can also have any size/shape. While a single-lobed (e.g., oval, spherical, racetrack, etc.) configuration is depicted for exemplary purposes, in various other embodiments, expandable structure 110 can be formed with a dual-lobed ("peanut shaped") configuration, or any other desired configuration.

Inflation fluid can be received by bone tamp 100 via an optional connector 130 (e.g., a Luer Lock fitting) at the proximal end of shaft 120 and can then be delivered to expandable structure 110 via shaft 120. Note that while connector 130 is depicted as a "Y" connecter (i.e., two fittings or ports) for exemplary purposes, connector 140 can take any shape and can include any number of fittings.

In various other embodiments, bone tamp 100 can further include an optional inner shaft 125. Expandable structure 110 can be coupled between outer shaft 120 and inner shaft 125, and inflation fluid can be delivered to expandable structure 110 through a lumen defined between outer shaft 120 and inner shaft 125. Alternatively, inflation fluid can be delivered to expandable structure 110 through inner shaft 125.

In various embodiments, shaft 120 (and optional inner shaft 125 if present) can be formed from any material (or combination of materials) that can take the desired shaft shape, such as silicone, polyvinyl chloride, latex rubber, polyethylene, polyurethane, Nitinol, or stainless steel, among others. In some embodiments, optional inner shaft 125 can be formed from a material configured to provide stiffening support to bone tamp 100 (i.e., shaft 120 and/or expandable structure 110).

In various other embodiments, an optional stiffening stylet 126 (e.g., stainless steel, Nitinol, or any other supportive material) can be removably or permanently inserted into shaft 120 (or optional inner shaft 125, if present) to provide some additional rigidity to bone tamp 100 (i.e., shaft 120/125 and/or expandable structure 110). In various embodiments, stylet 126 can include a cap or cover 126C for securing and sealing to connector 130 (e.g., via a threaded or locking interface).

In another embodiment, one or more radiopaque markers 120M can be placed at one or more locations on expandable bone tamp 100 to assist in visualization of expandable bone tamp 100 during a surgical procedure. Note that although two markers 120M positioned at the proximal and distal ends of expandable structure 110 are shown for exemplary purposes, in various other embodiments, markers 120M can additionally or alternatively be placed at any number of locations on expandable bone tamp 100. In various other embodiments, some or all of shaft 120 and/or some or all of expandable structure 110 can be formed from or can incorporate radiopaque materials, markings, or structures.

In various embodiments, kit 101 can further include optional additional instruments 150, such as an access cannula 151 sized to receive cannula 140, an introducer, guide pin, drill, curette, access needle, and/or material delivery system, among others (only access cannula 151 is shown for clarity). In various other embodiments, kit 101 can further include optional directions for use 160 that provide instructions for using expandable bone tamp 100, cannula 140, and optional additional instruments 150 (e.g., instructions for performing a surgical procedure using expandable bone tamp 100 cannula 140, such as described with respect to FIGS. 2A-2F and 3A-3G, below).

Figure 2A:
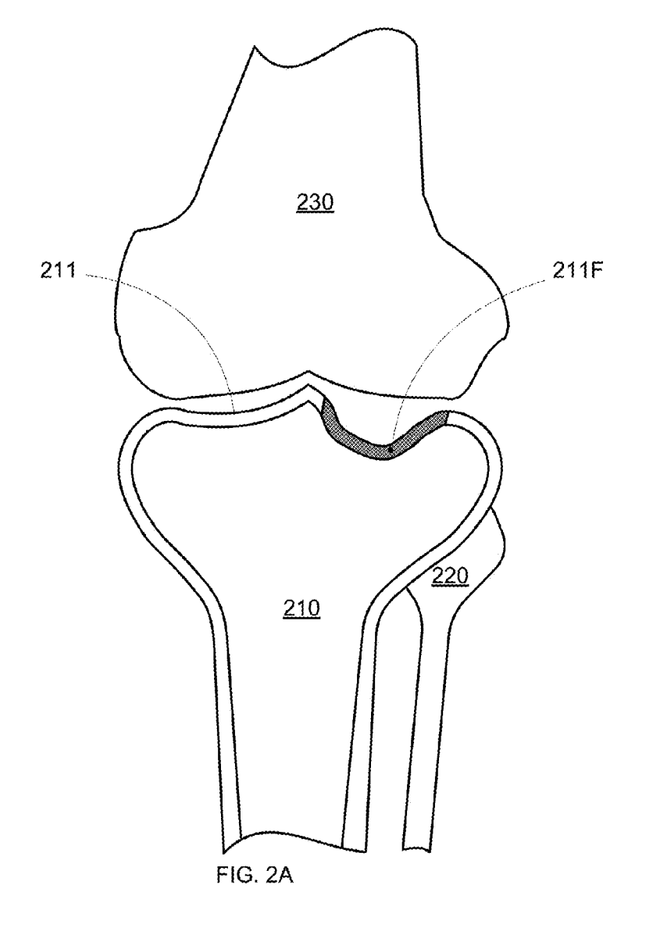
FIGS. 2A-2F show an exemplary surgical procedure that uses the kit of FIG. 1 to perform directional bone tamping.
Figure 2B:
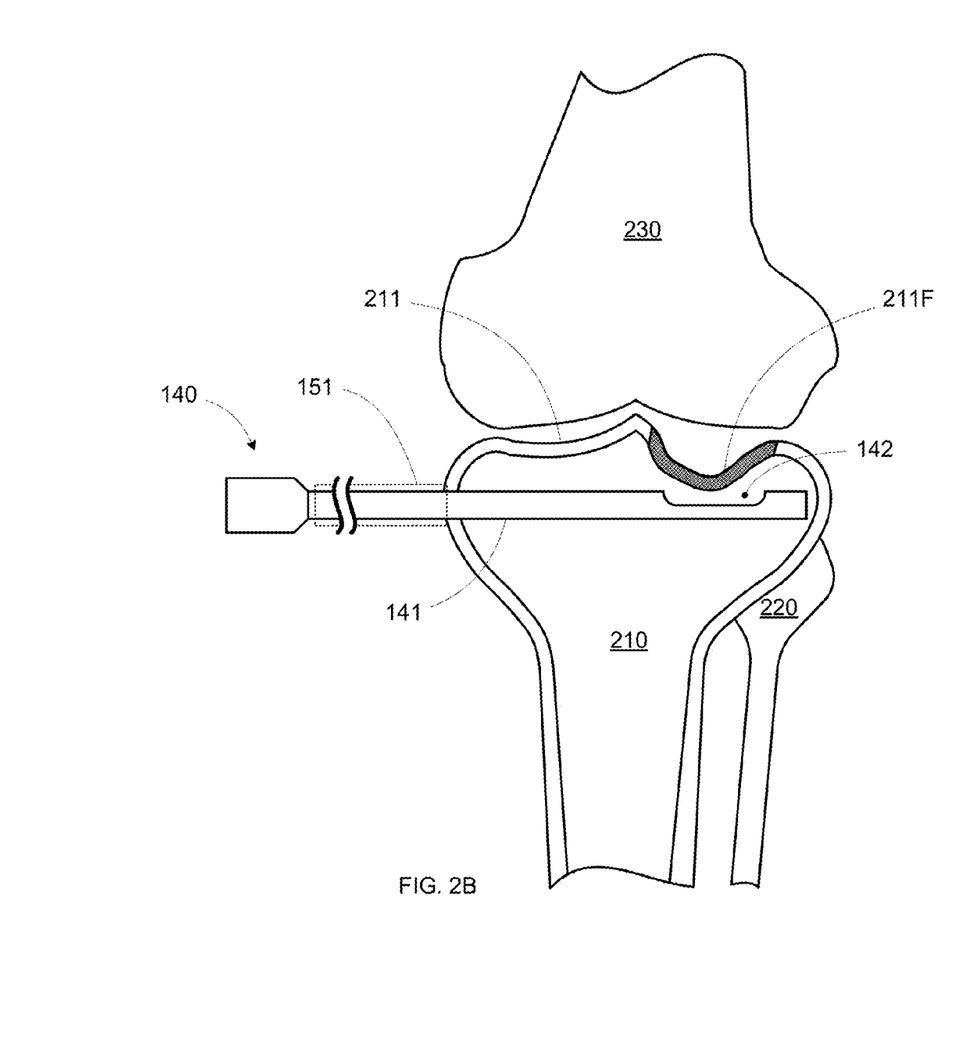

FIGS. 2A-2F show an exemplary minimally invasive surgical procedure using kit 101 shown in FIG. 1 to treat a tibial plateau fracture. FIG. 2A shows a sample tibial plateau fracture 211F in the tibial plateau 211 of a tibia 210. In FIG. 2B, cannula 140, as described with respect to FIG. 1, is introduced into tibia 210, such that side port 142 of cannula 140 is aligned with fracture 211F. Note that while cannula 140 is depicted as being directly positioned within tibia 210 for exemplary purposes, in various other embodiments, an optional access cannula 151 (shown in dotted outline) can be docked with tibia 210, and cannula 140 can be positioned through cannula 151.

Note further that although a contralateral approach to fracture 211F is depicted for exemplary purposes, cannula 140 can be positioned via any desired path to provide access to fracture 211F, including ipsilateral, medial, anterior, posterior, top-down, or oblique approaches.

Figure 2C:
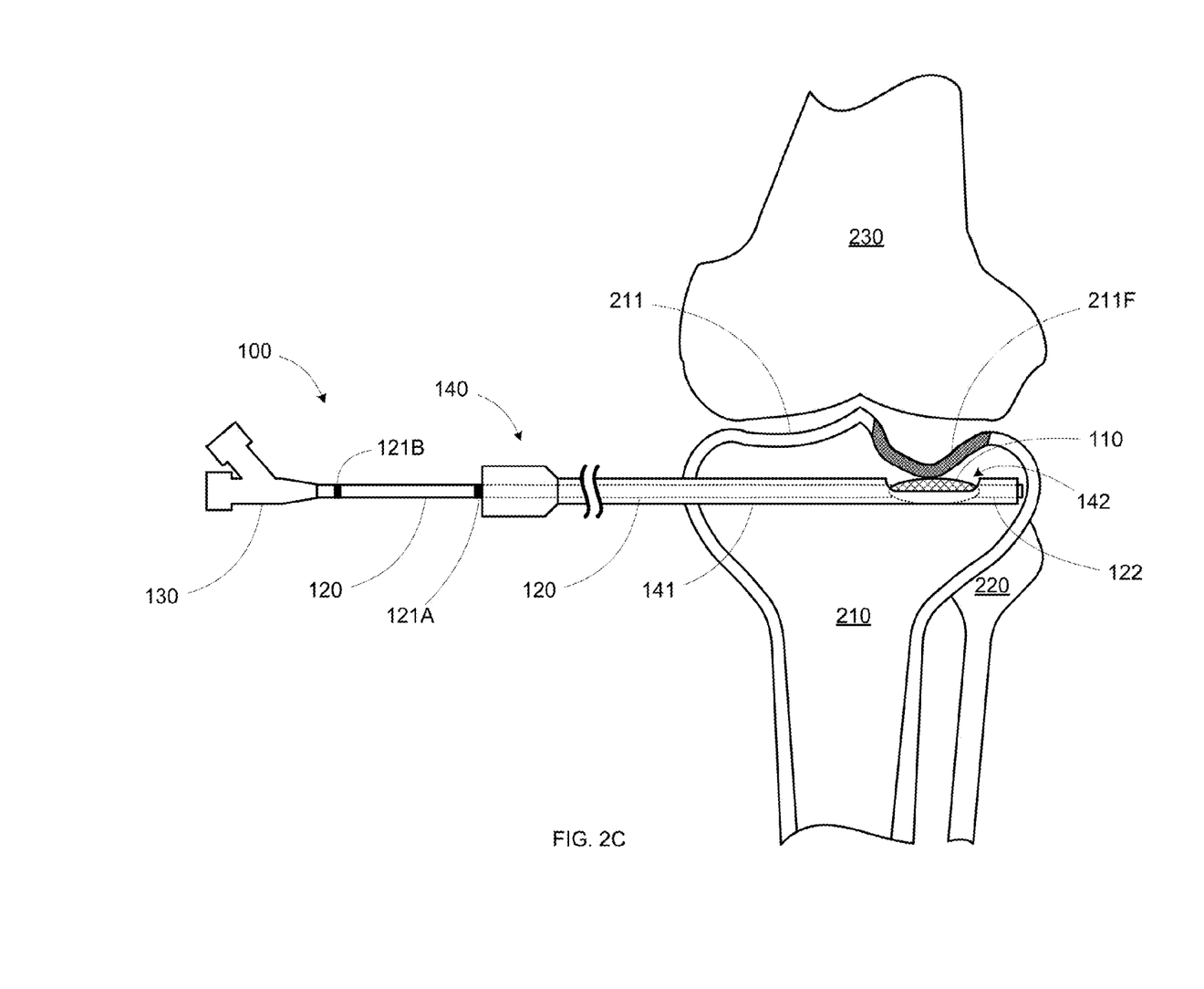

Once cannula 140 is positioned properly, expandable bone tamp 100, as described in FIG. 1, is inserted into lumen 140L of cannula 140 via proximal opening 144. Bone tamp 100 is advanced until expandable structure 110 is substantially aligned with side port 142, as shown in FIG. 2C. Note that this alignment of expandable structure 110 with side port 142 can be facilitated by the presence of positioning feature 121A (e.g., alignment of positioning feature 121A with the proximal end of cannula 140 can indicate when expandable structure 110 is correctly positioned alongside side port 142). Note further that, if present, optional elongate distal tip 122 of bone tamp 100 can extend deeply into the portion of cannula 140 distal to side port 142.

Figure 2D:
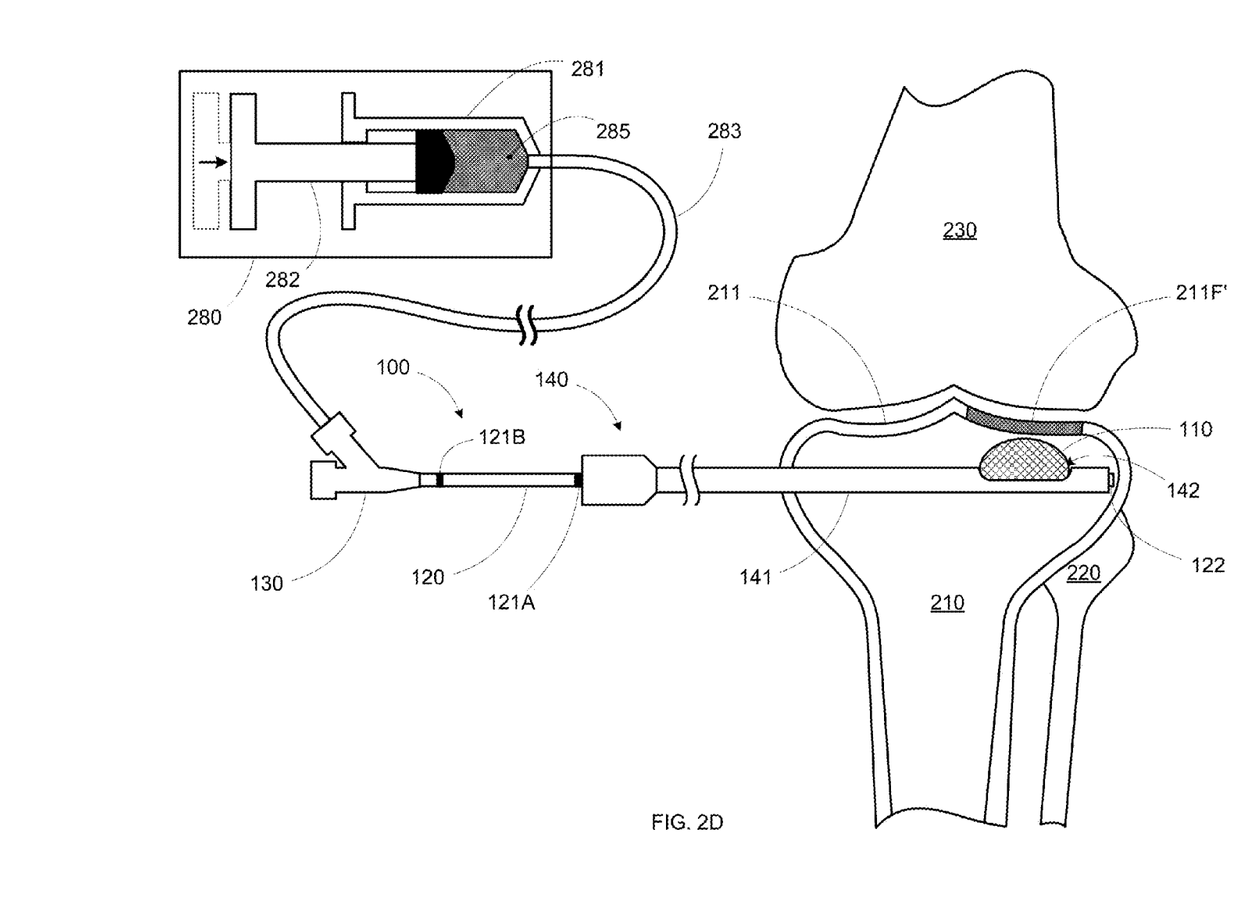

Then, in FIG. 2D, expandable structure 110 is expanded to restore fracture 211F (restored fracture designated as 211F'). For exemplary purposes, expandable structure 110 is depicted as an inflatable structure, wherein an inflation mechanism 280 is coupled to expandable bone tamp 100 by a flow channel 283 (e.g., flexible tubing). For exemplary purposes, inflation mechanism 280 is depicted as a syringe having a plunger 282 for expressing inflation fluid 285 (e.g., saline solution, air, contrast solution, or any other fluid) from a barrel 281. Note that in various other embodiments, inflation mechanism 280 can be any system for delivering inflation, such as a syringe, pump, or compressed gas system, among others. Furthermore, in various other embodiments, inflation mechanism 280 can be directly connected to expandable bone tamp 100.

Inflation mechanism 280 delivers inflation fluid 285 through flow channel 283, connector 130, and shaft 120 to expandable structure 110, thereby causing expandable structure 110 to expand through side port 142 of cannula 140. Side port 142 causes expandable structure 110 to expand mainly in the direction of fracture 211F to compress cancellous bone to create a cavity and/or restore the cortical bone profile of tibial plateau 211.

Note that in some embodiments, the structural stability of bone tamp 100 within cannula 140 as it is expanded out through side port 142 can be enhanced by the presence of optional elongate distal tip 122. Specifically, the extended engagement of elongate distal tip 122 with the portion of cannula 140 distal to side port 142 ensures that both the proximal and distal ends of expandable structure 110 are securely held within cannula 140 during expansion. In general, sufficient structural retention can be provided if elongate distal tip 122 has a length L2 at least one half the length L1 of expandable structure 110 (as shown in FIG. 1), although in various embodiments length L2 can be less than one half the length of expandable structure 110 (if, for example, optional inner shaft 125 and/or optional stylet 126 provide sufficiently enhanced structural rigidity along the longitudinal axis of bone tamp 100).

Figure 2E:
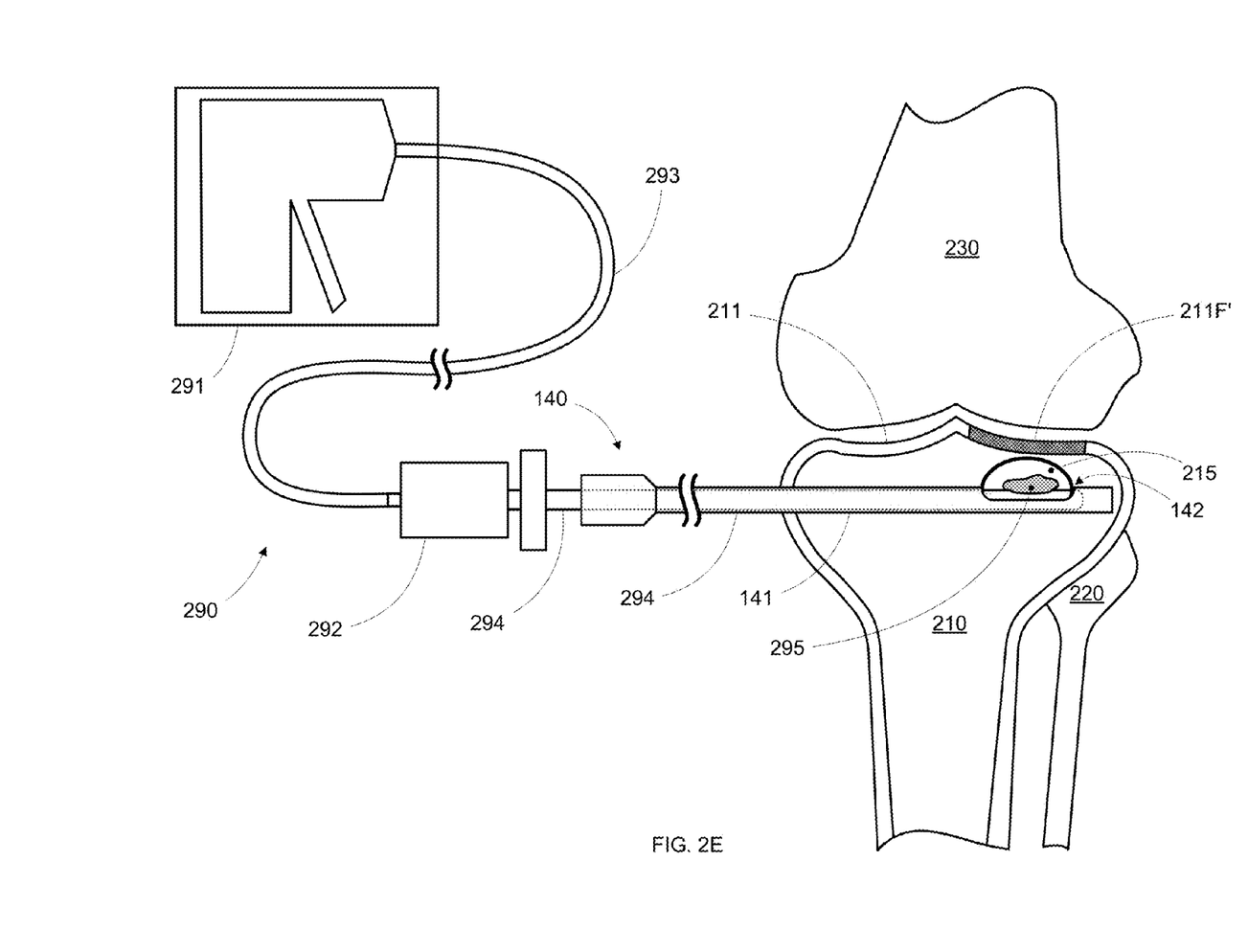

Once inflatable structure 110 has been expanded to a desired volume and/or a desired fracture restoration has been achieved in tibia 210, expandable structure 110 is returned to its unexpanded state, and bone tamp 100 is removed from cannula 140. Bone filler material (e.g., PMMA) can be delivered into the resulting cavity 215 formed by expandable structure 110. As shown in FIG. 2E, a delivery nozzle 294 can be inserted through cannula 140 such that a delivery port is aligned with cavity 215. In some embodiments, a quantity of bone filler material 295 can be housed in a cartridge 292 attached to delivery nozzle 294. A hydraulic actuator 291 can then be used to remotely express bone filler material 295 from cartridge 292 via a hydraulic line 293 (e.g., cartridge 292 can include a piston that is driven by the hydraulic pressure supplied by hydraulic line 293).

Note, however, that in various other embodiments, bone filler material 295 can be delivered to cavity 215 in any number of different ways (e.g., a high pressure cement delivery pump that delivers the cement to nozzle 294 through a flexible line, or a syringe or other delivery device filled with bone filler material 295 that is attached directly to nozzle 294, or even directly to cannula 140). In various other embodiments, cannula 140 can be removed prior to delivery of bone filler material 295. In addition, in various other embodiments, bone filler material 295 can be delivered in multiple portions of the same or different materials (e.g., a bone cement followed by a biologic agent).

Figure 4A:
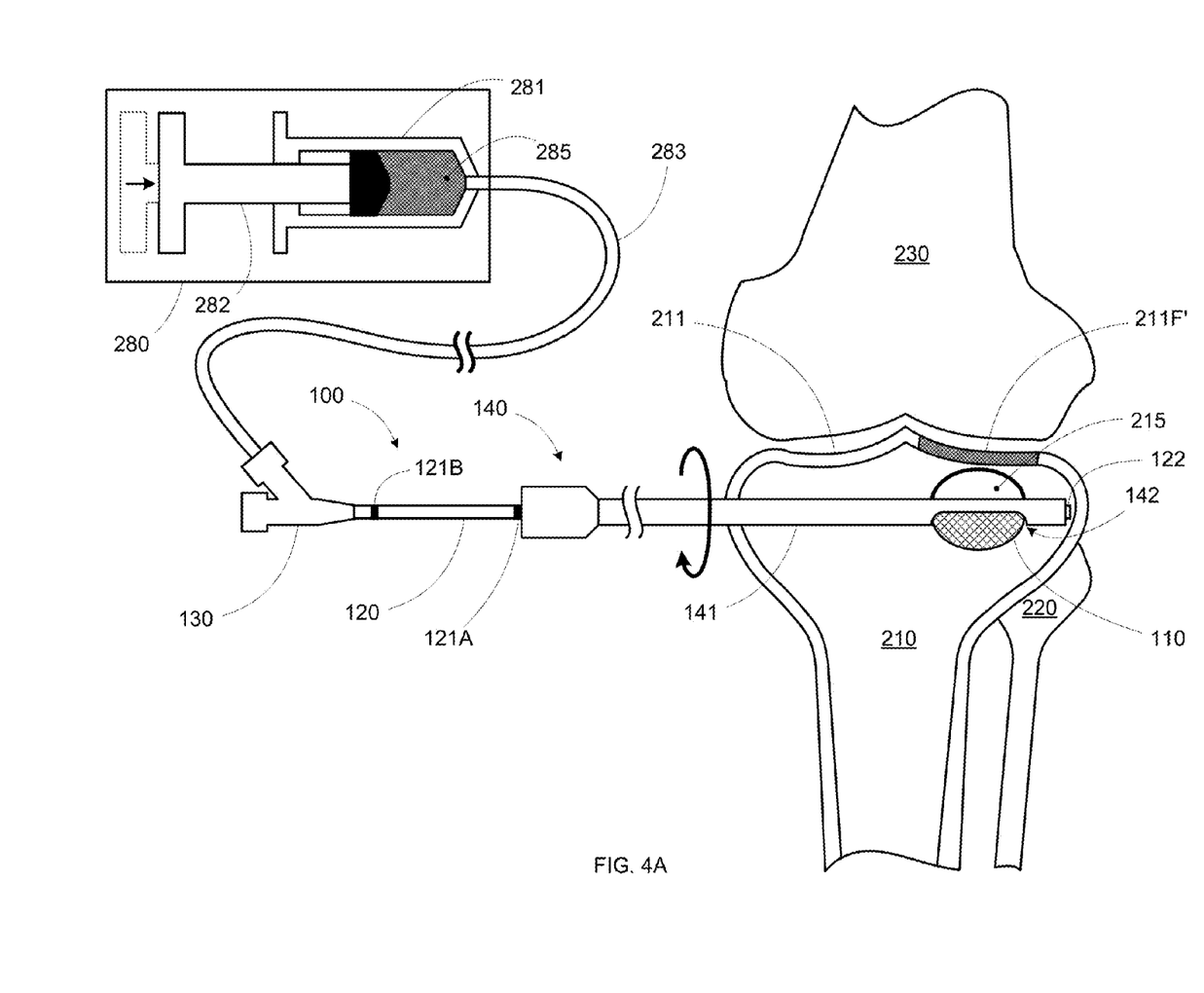
FIGS. 4A-4B show another exemplary surgical procedure using the kit of FIG. 1.
Figure 4B:
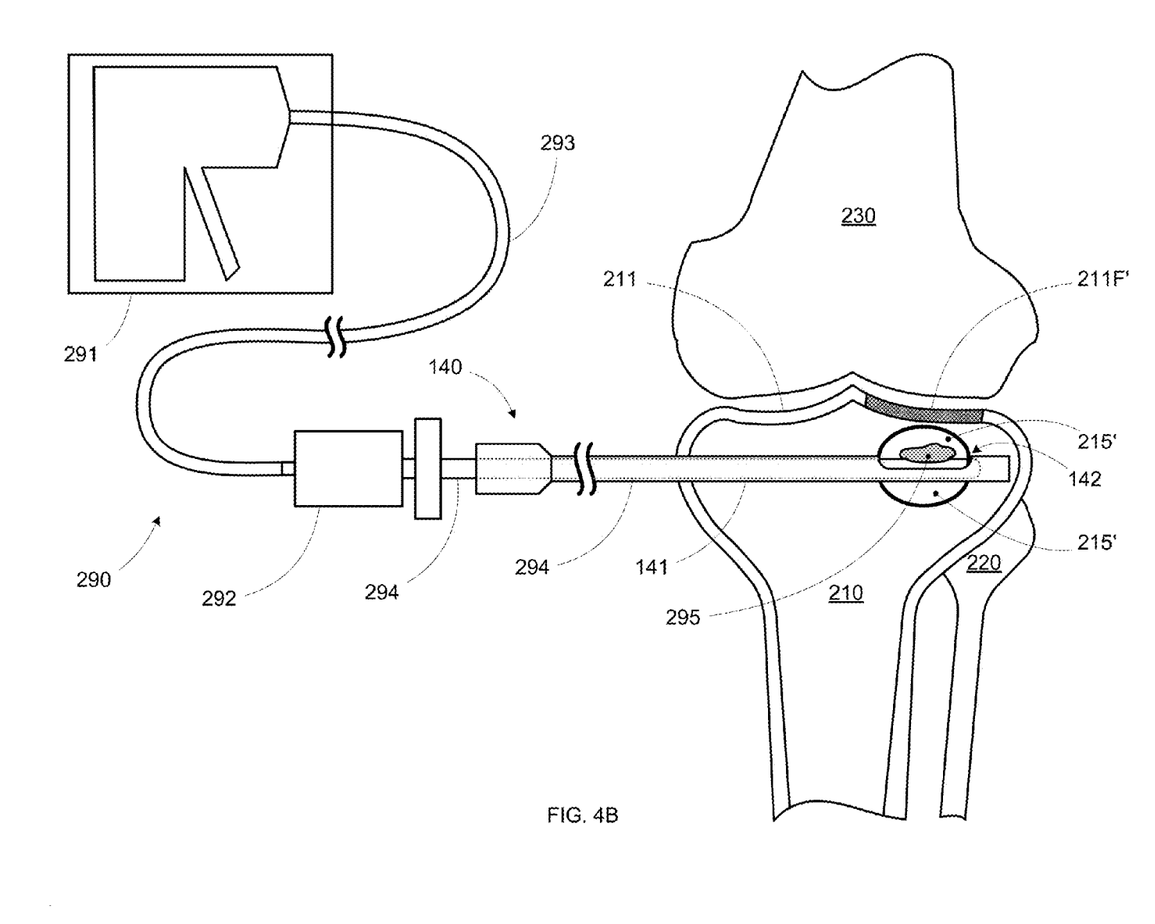

Note that in some embodiments, expandable element 110 can be expanded multiple times, and optionally in multiple orientations, to provide a desired fracture reduction and/or cavity creation. For example, in FIG. 4A, cannula 140 is rotated by a desired amount (e.g., roughly 180° to orient side port 142 substantially inferior to cavity 215) and expandable structure 110 is re-expanded. In this manner, a larger cavity 215' is ultimately provided as shown in FIG. 4B to allow for an increased volume of bone filler material 295 to be delivered to the fracture region.

Figure 2F:
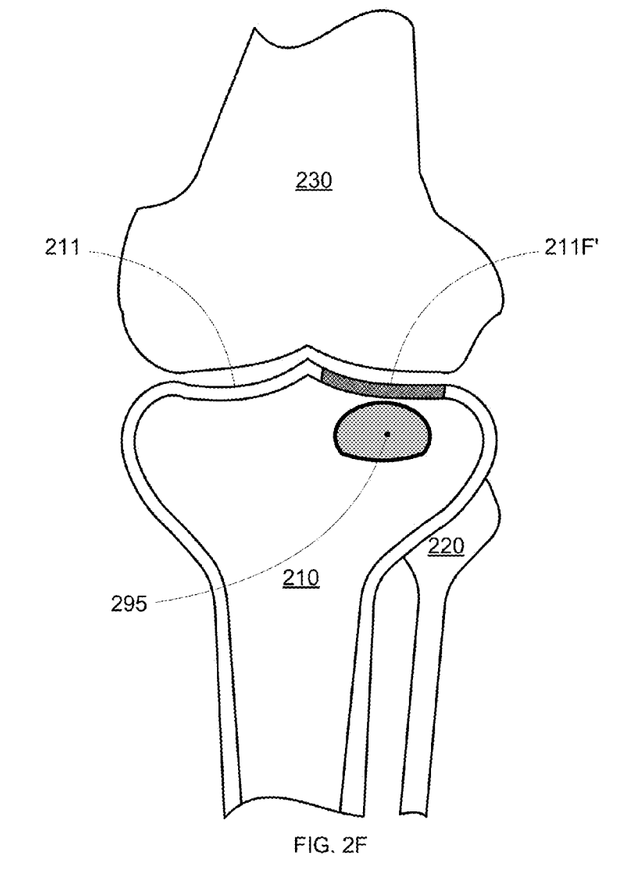

Once the filling operation(s) is complete, delivery nozzle 294 and cannula 140 are removed from tibia 210 (and the patient's body) as shown in FIG. 2F. Upon hardening, bone filler material 295 provides structural support for restored fracture 211F', thereby substantially restoring the structural integrity of tibial plateau 211 and the proper musculoskeletal alignment of the knee. In this manner, the pain and attendant side effects of a tibial plateau fracture can be addressed by a minimally invasive surgical procedure.

Figure 3A:
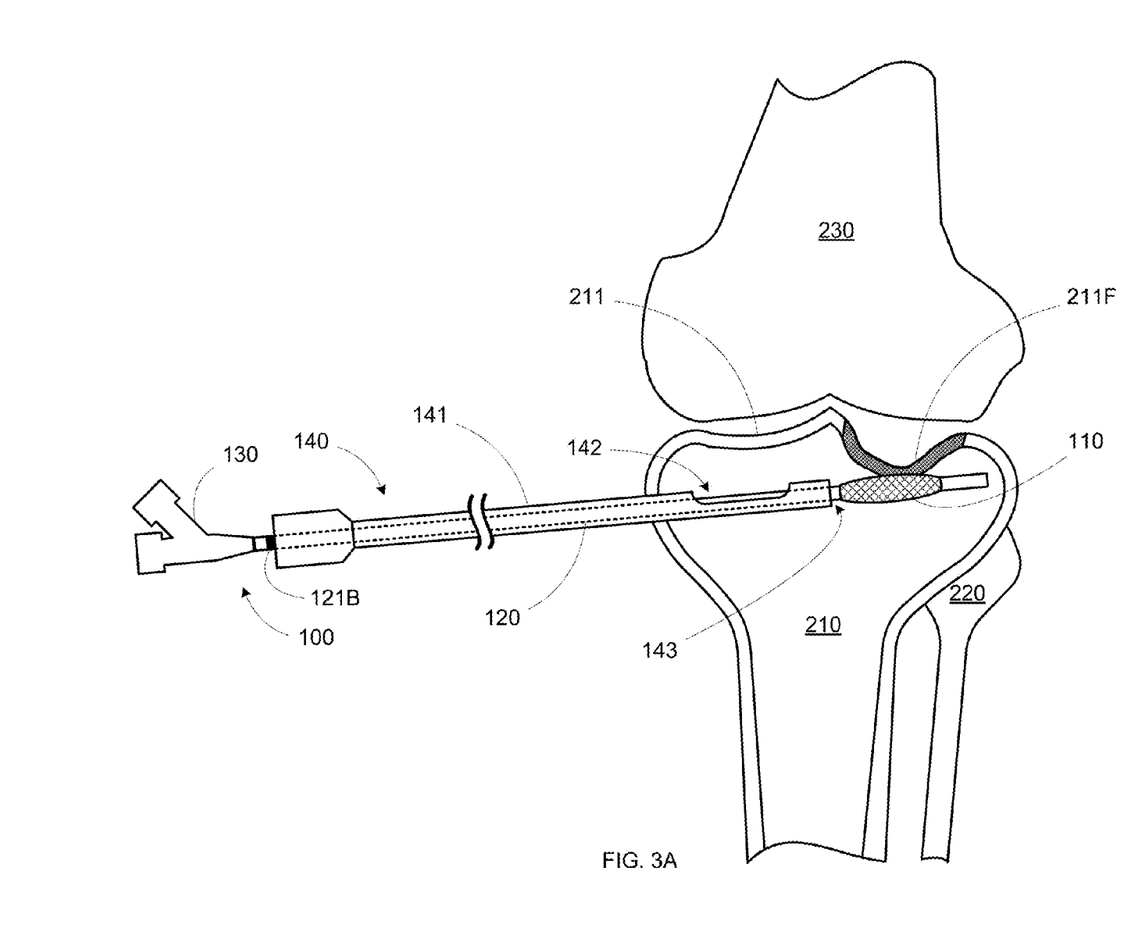
FIGS. 3A-3B show another exemplary surgical procedure that uses the kit of FIG. 1 to perform non-directional bone tamping.

Note that while a directional bone tamping procedure is described with respect to FIGS. 2A-2F, expandable bone tamp 100 and cannula 140 allow a non-directional bone tamping procedure using those same instruments to be performed if desired by the physician. For example, in FIG. 3A shows an alternative placement of cannula 140 and expandable bone tamp 100 in tibia 210. In contrast to the placement in FIGS. 2B-2D in which side port 142 is positioned close to fracture 211F, in FIG. 3A cannula 140 is oriented to allow bone tamp 100 to direct expandable structure 110 out distal opening 143 of cannula 140 towards fracture 211F.

Just as described with respect to the alignment of expandable structure 110 with side port 142 in FIG. 2C, the extension of expandable structure 110 beyond distal opening 143 shown in FIG. 3A can be facilitated by the presence of positioning feature 121B (e.g., alignment of positioning feature 121B with the proximal end of cannula 140 can indicate when expandable structure 110 is completely outside of cannula 140).

Figure 3B:
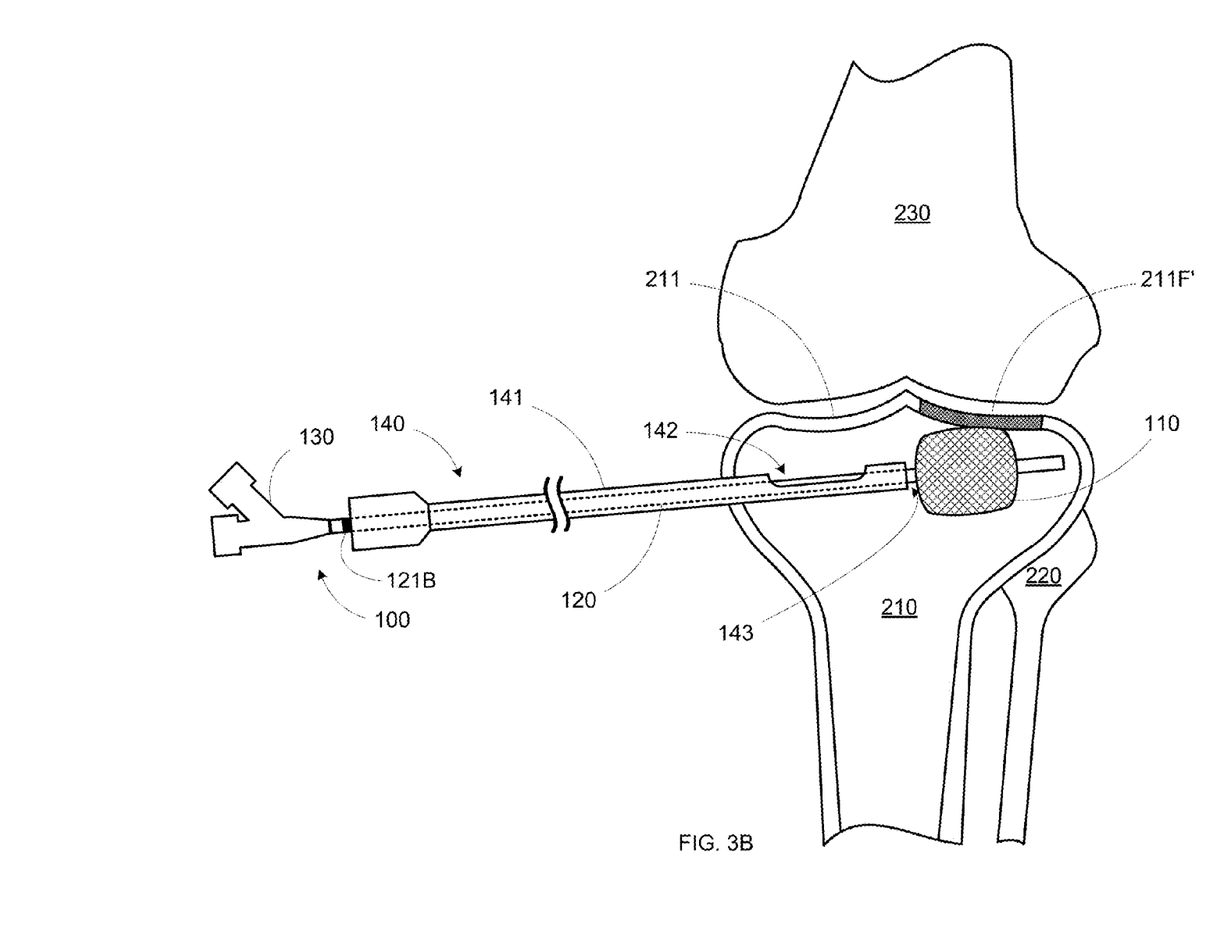

Then, as shown in FIG. 3B, expandable structure 110 can be expanded non-directionally to restore fracture 211F (restored fracture designated as 211F'). In a manner similar to that described with respect to FIG. 2D, the expansion of expandable structure 110 in FIG. 3B compresses cancellous bone and/or restores the cortical bone profile of tibial plateau 211. Bone tamp 100 can then be removed and bone filler material can be delivered to the fracture region to stabilize the reduced fracture 211F', as similarly described with respect to FIGS. 2E-2F.

In this manner, the combination of bone tamp 100 and cannula 140 enable either directional or non-directional bone manipulation to be applied to the target surgical location, without requiring any additional instruments.

Note that although treatment of a tibial plateau fracture is depicted and described for exemplary purposes, expandable bone tamp 100 and cannula 140 can be similarly used in any other target surgical location in or around bone, such as in a vertebral compression fracture, a proximal humerus fracture, a distal radius fracture, a calcaneus fracture, or a femoral head fracture, among others. Various other usages will be readily apparent.

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The invention claimed is:

1. A system for performing a surgical procedure, the device comprising:
    a cannula comprising a sidewall, the sidewall defining an open proximal end, an open distal end, and an inner lumen between the open proximal end and the open distal end, wherein the sidewall further defines a partial circumferential opening between the open proximal end and the open distal end;
    a material delivery nozzle sized to fit at least partially through the cannula; and
    an expandable bone tamp defining a longitudinal axis and comprising an elongate shaft carrying an expandable structure and an elongate distal tip defining a length along the longitudinal axis, the expandable structure defining a length along the longitudinal axis, wherein the length of the elongate distal tip is at least half of the length of the expandable structure,
    wherein the expandable structure is sized to fit through the inner lumen when in an unexpanded state,
    wherein the elongate shaft is sized to deliver the expandable structure from the open proximal end, through the inner lumen, and out the open distal end, and
    wherein the material delivery nozzle comprises a closed distal tip and at least one sidewall opening to allow passage of bone filler material out from within the material delivery nozzle.

2. The system of claim 1, wherein the expandable structure comprises an inflatable structure.

3. The system of claim 2, wherein the elongate shaft comprises a catheter defining an interior lumen,
    wherein the expandable bone tamp further comprises an inner shaft at least partially within the interior lumen, and
    wherein the inflatable structure is coupled between a distal end region of the catheter and a distal end region of the inner shaft.

4. The system of claim 3, wherein the expandable bone tamp further comprises a stiffening stylet sized to fit within the inner shaft.

5. The system of claim 1, wherein the expandable bone tamp further comprises a first marker for indicating at least one of alignment and orientation of the expandable structure relative to the partial circumferential opening.

6. The system of claim 5, wherein the expandable bone tamp further comprises a second marker for indicating extension of the expandable structure past the open distal end of the cannula.

7. The system of claim 5, wherein the first marker comprises a marking on the elongate shaft.

8. The system of claim 5, wherein the first marker comprises a positioning element coupled to the elongate shaft, the positioning element being sized to prevent further entry of the elongate shaft into the cannula when alignment of the expandable structure with the inflatable structure is achieved.

9. The system of claim 1, further comprising at least one of an access cannula sized to accept the cannula, an introducer, a guide pin, a drill, a curette, and an access needle.

10. The system of claim 1, further comprising instructions for performing the surgical procedure within bone using the cannula and the expandable bone tamp.

11. The system of claim 1, wherein the sidewall further defines a second partial circumferential opening between the open proximal and the open distal end.

12. A surgical kit comprising:
    a cannula having an open distal end, an open proximal end, and at least one side port between the open distal end and the open proximal end;
    a material delivery nozzle sized to fit at least partially through the cannula; and
    a bone tamp comprising an elongate shaft and an expandable element coupled to a proximal end region of the elongate shaft,
    wherein the expandable element is sized to pass through the cannula when in an unexpanded state,
    wherein the at least one side port is sized to allow expansion of at least a portion of the expandable element therethrough,
    wherein the material delivery nozzle comprises a closed distal tip and at least one sidewall opening to allow passage of bone filler material out from within the material delivery nozzle, and
    wherein a length of the elongate shaft is greater than a length of the cannula.

13. The surgical kit of claim 12, wherein the expandable element comprises an inflatable structure.

14. The surgical kit of claim 12, wherein the bone tamp further comprises a first marker for indicating alignment of the expandable element with the at least one side port.

15. The surgical kit of claim 12, further comprising instructions for performing a surgical procedure within bone using the cannula and the bone tamp.

* * * * *